(12) United States Patent
Küebler

(10) Patent No.: US 8,317,739 B2
(45) Date of Patent: Nov. 27, 2012

(54) SURGICAL SYSTEM FOR CONTROLLING FLUID

(75) Inventor: Christoph Küebler, Oberkochen (DE)

(73) Assignee: Carl Zeiss Meditec AG, Oberkochen (DE)

( * ) Notice: Subject to any disclaimer, the term of this patent is extended or adjusted under 35 U.S.C. 154(b) by 178 days.

(21) Appl. No.: 12/740,213

(22) PCT Filed: Nov. 4, 2008

(86) PCT No.: PCT/EP2008/009264
§ 371 (c)(1),
(2), (4) Date: Jul. 2, 2010

(87) PCT Pub. No.: WO2009/059732
PCT Pub. Date: May 14, 2009

(65) Prior Publication Data
US 2010/0280439 A1    Nov. 4, 2010

(30) Foreign Application Priority Data

Nov. 9, 2007 (DE) .......................... 10 2007 053 370

(51) Int. Cl.
*A61M 3/00* (2006.01)
*A61M 1/00* (2006.01)

(52) U.S. Cl. .......................................... 604/43; 604/35

(58) Field of Classification Search ............ 604/22, 604/35, 43–45, 289, 294
See application file for complete search history.

(56) References Cited

U.S. PATENT DOCUMENTS

| | | | |
|---|---|---|---|
| 4,832,685 A | 5/1989 | Haines | |
| 5,167,620 A | 12/1992 | Ureche et al. | |
| 5,261,883 A * | 11/1993 | Hood et al. | 604/153 |
| 5,697,898 A | 12/1997 | Devine | |
| 5,733,256 A | 3/1998 | Costin | |
| 6,261,283 B1 | 7/2001 | Morgan et al. | |
| 6,283,937 B1 | 9/2001 | Takamatsu et al. | |
| 6,740,074 B2 | 5/2004 | Morgan et al. | |
| 2003/0146299 A1 | 8/2003 | Suzuki et al. | |

OTHER PUBLICATIONS

English translation of the International Preliminary Report on Patentability for corresponding PCT Appl. No. PCT/EP2008/009264, dated Jun. 1, 2010.
English translation of the International Search Report for corresponding PCT Appl. No. PCT/EP2008/009264, dated Mar. 25, 2009.

* cited by examiner

*Primary Examiner* — Nicholas Lucchesi
*Assistant Examiner* — Nathan R Price
(74) *Attorney, Agent, or Firm* — Fish & Richardson P.C.

(57) ABSTRACT

The invention relates to a surgical system for controlling a fluid. The system includes an irrigation line, which is connected at one end to a first fluid container for holding irrigation fluid, and which is connected at another end to a surgical handpiece. The system also includes an aspiration inlet line, which is provided from the surgical handpiece to an inlet of a suction pump, such that fluid can be sucked through the handpiece by the suction pump. The system further includes a second fluid container for holding the irrigation fluid, and an aspiration ventilation line, which connects the second fluid container to the aspiration inlet line. In addition, the system includes a venting valve, which is provided in the aspiration ventilation line and which can be switched as a function of a fluid pressure in the aspiration inlet line. The second fluid container can be filled via a filling line. The filling line is connected at one end to the irrigation line, and the filling line has a flow element with a constant hydraulic resistance of between 0.5 and 50.0 mmHg/(ml/min).

20 Claims, 7 Drawing Sheets

Figure 1:
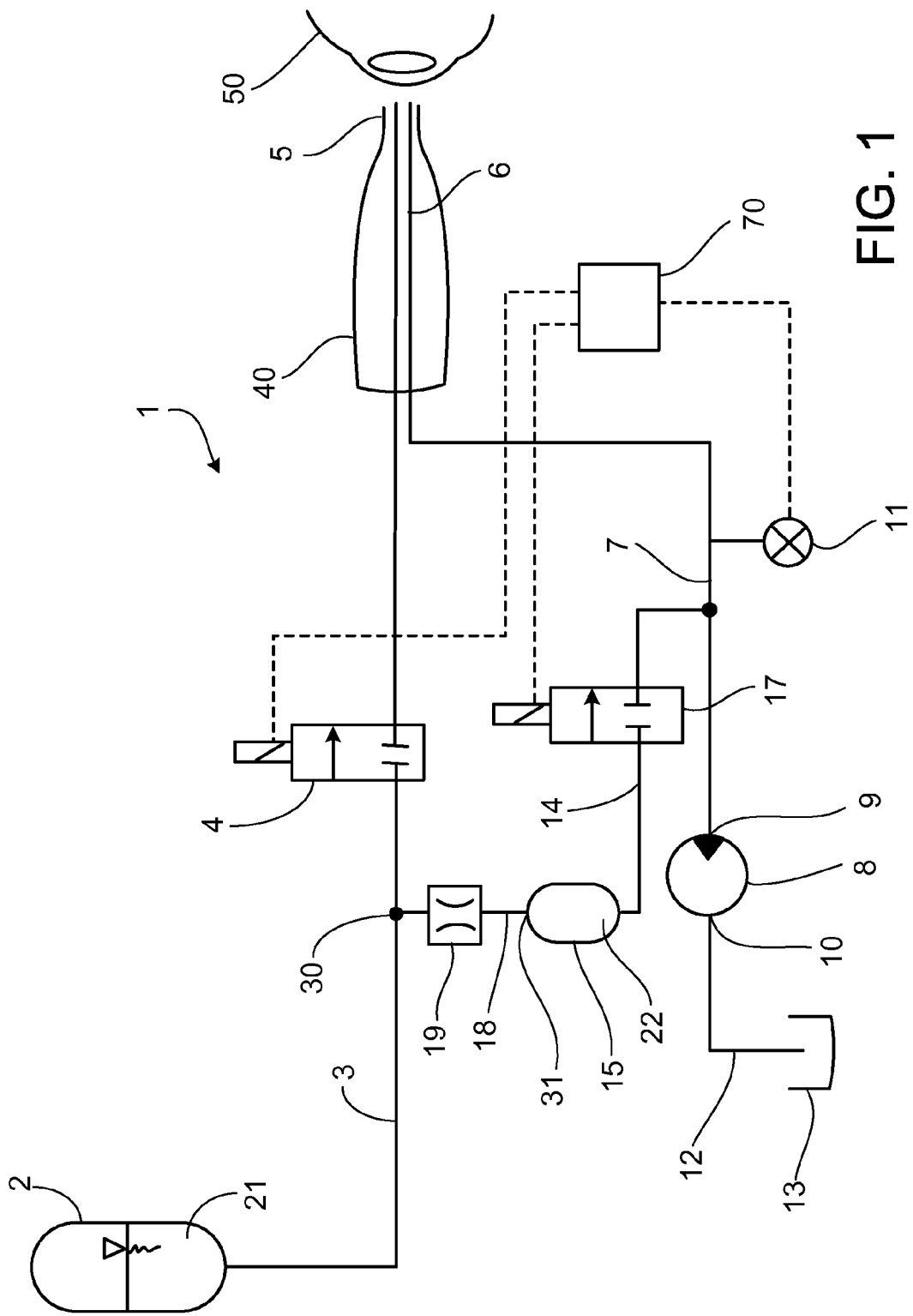

| Element | Length $l$ | internal diameter $di$ | wall thickness $h$ | elastic modulus | Poisson ratio | total hydraulic resistence | total hydraulic inductance | total hydraulic capacitance | phase velocity |
|---|---|---|---|---|---|---|---|---|---|
| unit | m | mm | mm | MPa | | mmHg/ml*min | mmHg*s/(ml/min) | (ml/min)/(mmHg/s) | m/sec |
| BSS hose | 2.00 | 3.20 | 0.80 | 1 | 0.30 | 0.10 | 0.0311 | 0.510 | 16 |
| IRR hose | 2.00 | 4.00 | 0.80 | 1 | 0.30 | 0.04 | 0.0199 | 1.010 | 14 |
| IRR handpiece | 0.10 | 1.00 | 0.30 | | | 0.51 | | | |
| ASP handpiece | 0.06 | 0.80 | 0.30 | | | 0.75 | | | |
| EYE R | | | | | | 31.90 | | | |
| EYE C | | | | | | | | 0.050 | |
| ASP hose | 2.00 | 1.80 | 1.00 | 3 | 0.30 | 0.97 | 0.0982 | 0.020 | 41 |

FIG. 7

SURGICAL SYSTEM FOR CONTROLLING FLUID

CROSS-REFERENCE TO RELATED APPLICATIONS

This application is the National Stage of International Application No. PCT/EP2008/009264, filed Nov. 4, 2008, which claims the benfit of German Application No. 10 2007 053 370.7, filed Nov. 9, 2007.

The invention relates to a surgical system and a method for controlling fluid during the treatment of cataract by phacoemulsification.

There are several surgical techniques for treatment of clouding of the lens, which is referred to in medicine as gray cataract. The most widely used technique is phacoemulsification, in which a thin tip is introduced into the diseased lens and is excited to vibration with ultrasound. In its immediate environment, the vibrating tip emulsifies the lens in such a way that the resulting lens fragments can be sucked through a line by a pump. When the lens has been completely emulsified, a new and artificial lens can be inserted into the empty capsular bag, such that a patient treated in this way can recover good visual acuity.

In phacoemulsification, a device is used that generally has a vibratable tip in a handpiece, a flushing line (irrigation line) for supplying irrigation fluid to the lens to be treated, and a suction line (aspiration line) for transporting emulsified lens fragments into a collecting vessel. During transport into the collecting vessel, it can happen that a lens fragment blocks the inlet area of the handpiece tip. With a suction pump running continuously, a vacuum, for example with a pressure of −700 mmHg, therefore builds up downstream in the aspiration line. If the blockage does not clear by itself after a certain period of time (occlusion blockade), it is necessary, for safety reasons, to compensate the underpressure in the aspiration line.

The prior art proposes various solutions for achieving such a pressure compensation. U.S. Pat. No. 4,832,685 describes the aspiration line being connected to the irrigation line, such that a pressure compensation is achieved by the irrigation fluid. A disadvantage of this is that the fluid present in the irrigation line is excited to pressure fluctuations, which continue through the irrigation line to the eye. This leads to a dangerous destabilization of the pressure in the anterior chamber of the eye, which can cause the eye to collapse. There is also a possibility of the capsular bag being drawn toward the tip of the handpiece and punctured by the tip. In addition to such damage of the capsular bag, it is also possible for a tip that has penetrated too deeply to damage the vitreous body lying behind the capsular bag. A further disadvantage of this system described in U.S. Pat. No. 4,832,685 is that, in this kind of fluid pressure compensation, contaminated fluid may flow from the aspiration line into the irrigation line. Consequently, such a surgical system can be used only for a single patient.

Another possibility is to perform pressure compensation by means of ambient air. In this case, air at atmospheric pressure is introduced into the aspiration line. An advantage of this is that it does not cause any pressure fluctuation in the irrigation line. However, the air introduced into the aspiration line changes the fluidic characteristics of the suction system, such that the air has to be pumped out of the aspiration line in order to once again obtain a dynamic suction pressure characteristic in the aspiration line.

U.S. Pat. No. 6,740,074 B2 and U.S. Pat. No. 6,261,283 propose withdrawing fluid from a collecting vessel arranged at the end of the aspiration line and introducing this fluid into the aspiration line. However, contaminated particles from the collecting vessel are introduced into the aspiration line in this solution, such that a system of this kind becomes unsterile and is suitable only for one patient, not for several patients.

It is therefore an object of the invention to make available a surgical system which permits rapid pressure compensation when there is an underpressure in the aspiration line, wherein no pressure fluctuations are induced in the eye, the fluidic characteristics in the aspiration line are not changed, a high degree of operational safety can be achieved, and no contaminated fluid reaches the irrigation line, such that the system can also be used for several patients. It is also an object of the invention to make available a method for operating a surgical system of this kind.

The object is achieved by a system having the features disclosed herein and by a method having the features disclosed herein.

The surgical system according to the invention for controlling a fluid has:
  an irrigation line, which is connected at one end to a first fluid container for holding irrigation fluid, and which is connected at another end to a surgical handpiece,
  an aspiration inlet line, which is provided from the surgical handpiece to an inlet of a suction pump, such that fluid can be sucked through the handpiece by the suction pump,
  a second fluid container for holding the irrigation fluid,
  an aspiration ventilation line, which connects the second fluid container to the aspiration inlet line,
  a venting valve, which is provided in the aspiration ventilation line and can be switched as a function of the fluid pressure in the aspiration inlet line,
  wherein the second fluid container can be filled via a filling line, wherein the filling line is connected at one end to the irrigation line, and wherein the filling line has a flow element with a constant hydraulic resistance of between 0.5 and 50 mmHg/(ml/min).

Such a system is advantageous since the flow element, with a hydraulic resistance of between 0.5 and 50 mmHg/(ml/min), provides a substantial attenuation of vibration for the fluid, starting from the flow element and proceeding along the filling line as far as the irrigation line and, within the irrigation line, as far as the eye. The hydraulic resistance is particularly preferably from 0.5 to 5.0 mmHg/(ml/min). In this way, the hydraulic internal diameter of the flow element is not too small, such that said flow element can be manufactured without great effort. When the venting valve is opened and a pressure compensation of the aspiration inlet line takes place, fluid is sucked out of the second fluid container in a very short time and fills the aspiration line. The flow element has the effect that the pressure fluctuation in the second fluid container cannot pass unimpeded to the irrigation line, and instead it is strongly attenuated on account of the relatively high hydraulic resistance of the flow element. The oscillation in the second fluid container is not kept completely away from the irrigation line by the flow element. It is still measurable in the irrigation line, but its amplitude is so low that there is never a danger of the eye collapsing.

A further advantage is that two fluid containers are used, not just one. In the event of an occlusion in the aspiration line, the system according to the invention allows fluid from the second fluid container to be guided through the aspiration ventilation line into the aspiration inlet line, if the venting valve has been suitably switched. Since the second fluid container contains sterile fluid, contamination of the aspiration line by the venting is ruled out. It is thus possible to use the surgical system on several patients who are treated in succession, without danger of contamination with previously introduced contaminants. By using a second fluid container, handling is also relatively simple and safe in practice. It suffices, for example, prior to the start of an operation, to fill only the first fluid container with irrigation fluid, or to check the filling level of the first fluid container, and subsequently to fill the second fluid container with this sterile fluid, and, by means of the oscillation-limiting flow element, this takes place automatically and with very low oscillation. It is not necessary for operating personnel to check whether the second fluid container is filled.

A further advantage is that the flow element does not have to be actuated and instead can act independently. This permits relatively simple and therefore rapidly responding safety logics for those valves that still have to be actuated. In addition, the use of the flow element avoids the costs of a switching valve that is susceptible to wear.

According to one embodiment of the invention, it is advantageous if the flow element, at a dynamic viscosity of the fluid of $\eta=0.001$ Ns/m$^2$, which is a standard value for an irrigation saline solution (hereinafter BSS solution), has a length passed through by the fluid of less than 100 mm with a hydraulic radius of less than 1.0 mm, preferably 0.7 mm. With these values, the required hydraulic resistance of 0.5 to 50 mmHg/(ml/min) can be achieved, the tolerance for the radius being relatively small, since the latter, according to Poiseuille's law, is included with the fourth power in the calculation of the hydraulic resistance. The flow element can preferably be designed as a line, channel, bore or diaphragm. The cross section is preferably round, although it can also be square, as in a channel in an injection molded part.

According to one embodiment of the invention, the second fluid container has a hydraulic capacitance of 0.05 to 0.2 (ml/min)/(mmHg/s). The hydraulic capacitance of the second fluid container is therefore only about one twentieth to one fifth of the hydraulic capacitance of an irrigation hose. The ability to achieve a suitable change in volume with a change in fluid pressure can be set relatively low. The reason for this is that only a small volume of fluid is stored in the second fluid container compared to the elastic irrigation line or has to be discharged during a venting procedure, since the hydraulic capacitance of the aspiration line is about a factor of 10 to 20 smaller than the hydraulic capacitance of the irrigation line.

It is advantageous if the hydraulic capacitance of the second fluid container is at least the same as or preferably more than twice the hydraulic capacitance of the aspiration inlet line. Upon pressure compensation in the aspiration line, fluid flows from the second fluid container into the evacuated aspiration line. Analogously to the discharging of an electrical capacitor, here too the fluid container empties as a function of time according to an exponential function. The emptying of the second fluid container or the pressure compensation in the aspiration inlet line takes place all the more quickly the greater the hydraulic capacitance of the second fluid container. It has been shown in practice that a satisfactory pressure compensation is achieved at a hydraulic capacitance of the second fluid container when this is at least equal to the hydraulic capacitance of the aspiration inlet line.

According to one embodiment, the filling line, at the other end, is coupled to the second fluid container by a mechanical or chemical connecting means or by a connection based on a thermal connecting method. This can, for example, involve clamping, bonding, welding and, particularly in the case of plastics, connection by means of polymerization or polycondensation.

The second fluid container is preferably tubular, for example designed as a hose like the filling line or aspiration ventilation line, thereby resulting in an inexpensive solution that is easy to implement. The hose also affords the advantage that it is elastically deformable not just within a limited area but about its entire circumference. Particularly preferably, at least part of the filling line, the second fluid container and at least part of the aspiration ventilation line are formed in one piece, thus permitting simple assembly in a cassette.

If the irrigation line has an irrigation valve, the latter can be brought into such a position that the irrigation line is interrupted. If the irrigation valve in the irrigation line is arranged between handpiece and filling line, the second fluid container can be filled particularly quickly with fluid from the first fluid container by way of the filling line. Since the irrigation valve is closed at the start of an operation, the second fluid container first fills on account of the hydrostatic pressure in the irrigation line. In addition, during filling of the second fluid container with the irrigation valve closed, no pressure fluctuations occur in that part of the irrigation line arranged between irrigation valve and handpiece. This ensures that no pressure fluctuations are induced in the eye during the filling of the second fluid container.

According to another embodiment of the invention, fluid can be carried off by the aspiration ventilation line at the bottom or near the bottom of the second fluid container. This ensures that the maximum available quantity of ventilating fluid can always be made available and, in addition, no air is fed into the aspiration inlet line when the container is filled.

The pressure sensor preferably detects the fluid pressure in the aspiration line close to the handpiece. In this way, when there is a break-up of an occlusion, the pressure change can be quickly detected because of the short distance from the handpiece tip to the pressure sensor and, therefore, the venting valve can be quickly triggered. Venting can be achieved especially quickly if the pressure sensor detects the fluid pressure in the aspiration line within the handpiece, preferably near the tip of the handpiece.

The object is further achieved by a method for controlling fluid when venting an aspiration inlet line in a surgical system of the kind described above, in which method the venting valve, when or after a predefined vacuum pressure has been reached in the aspiration inlet line, is switched such that fluid from the second fluid container is delivered from the aspiration ventilation line to the aspiration inlet line, and the second fluid container is filled with irrigation fluid from the first fluid container, wherein the irrigation fluid flows through the flow element in the filling line.

Figure 2:
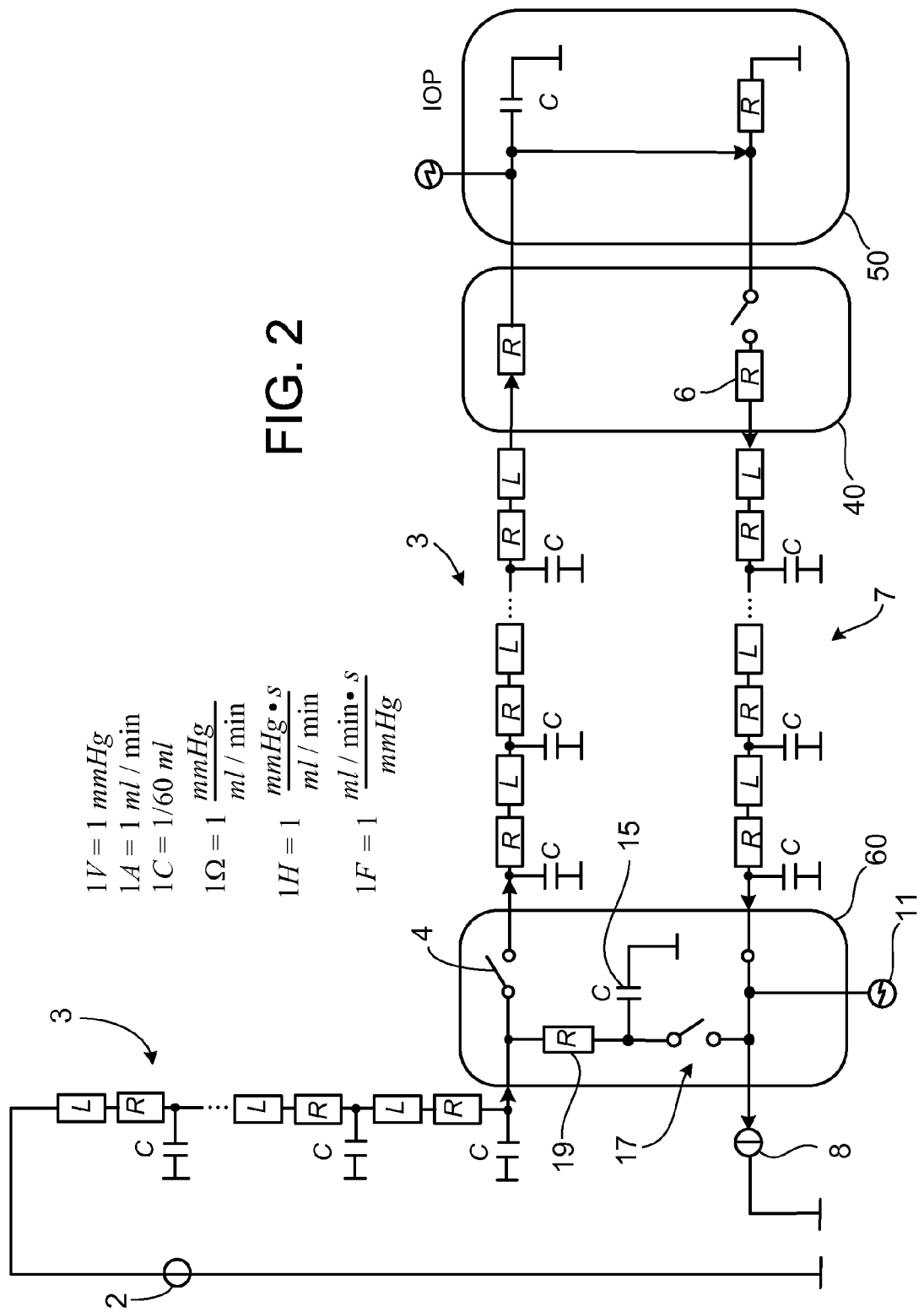
Figure 3C:
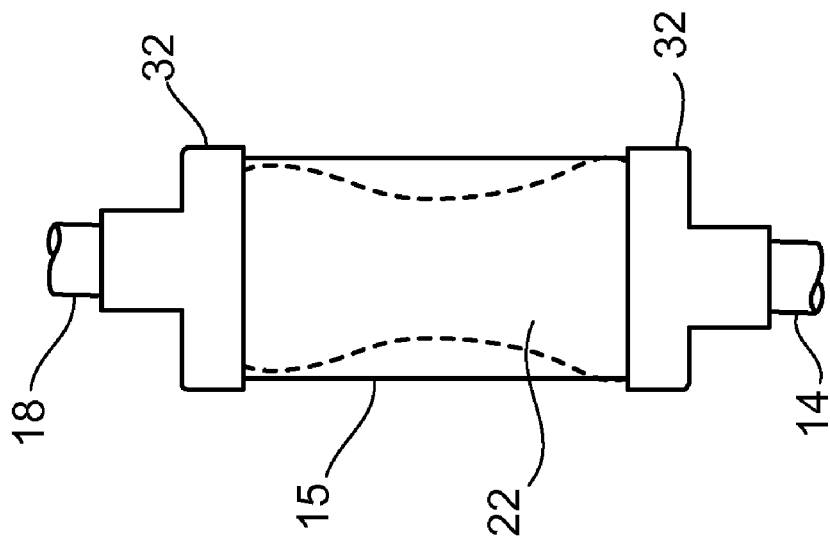
Figure 3B:
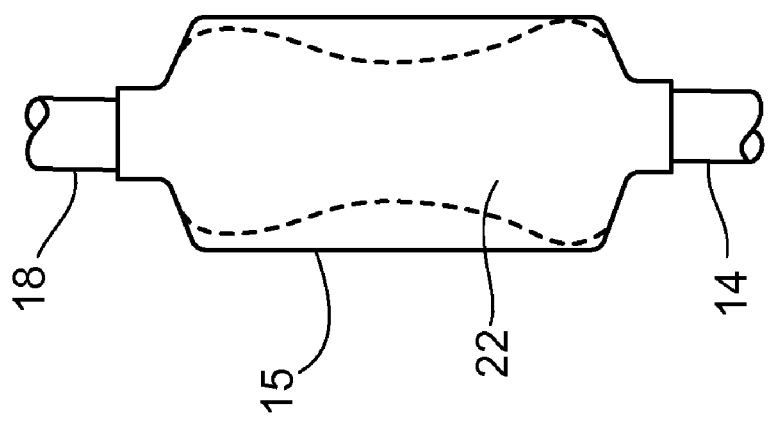
Figure 3A:
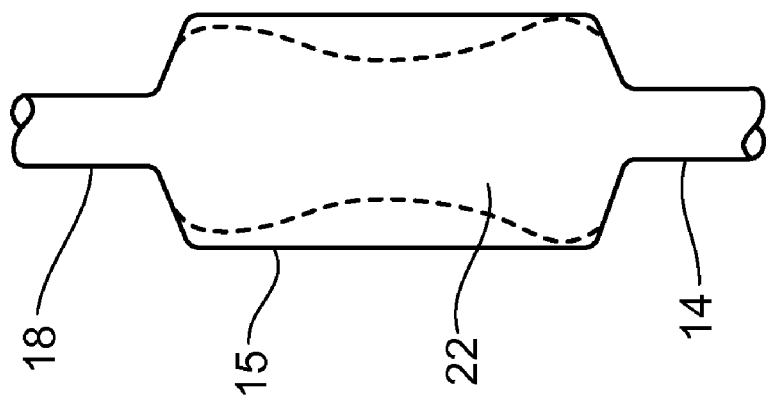
Figure 4:
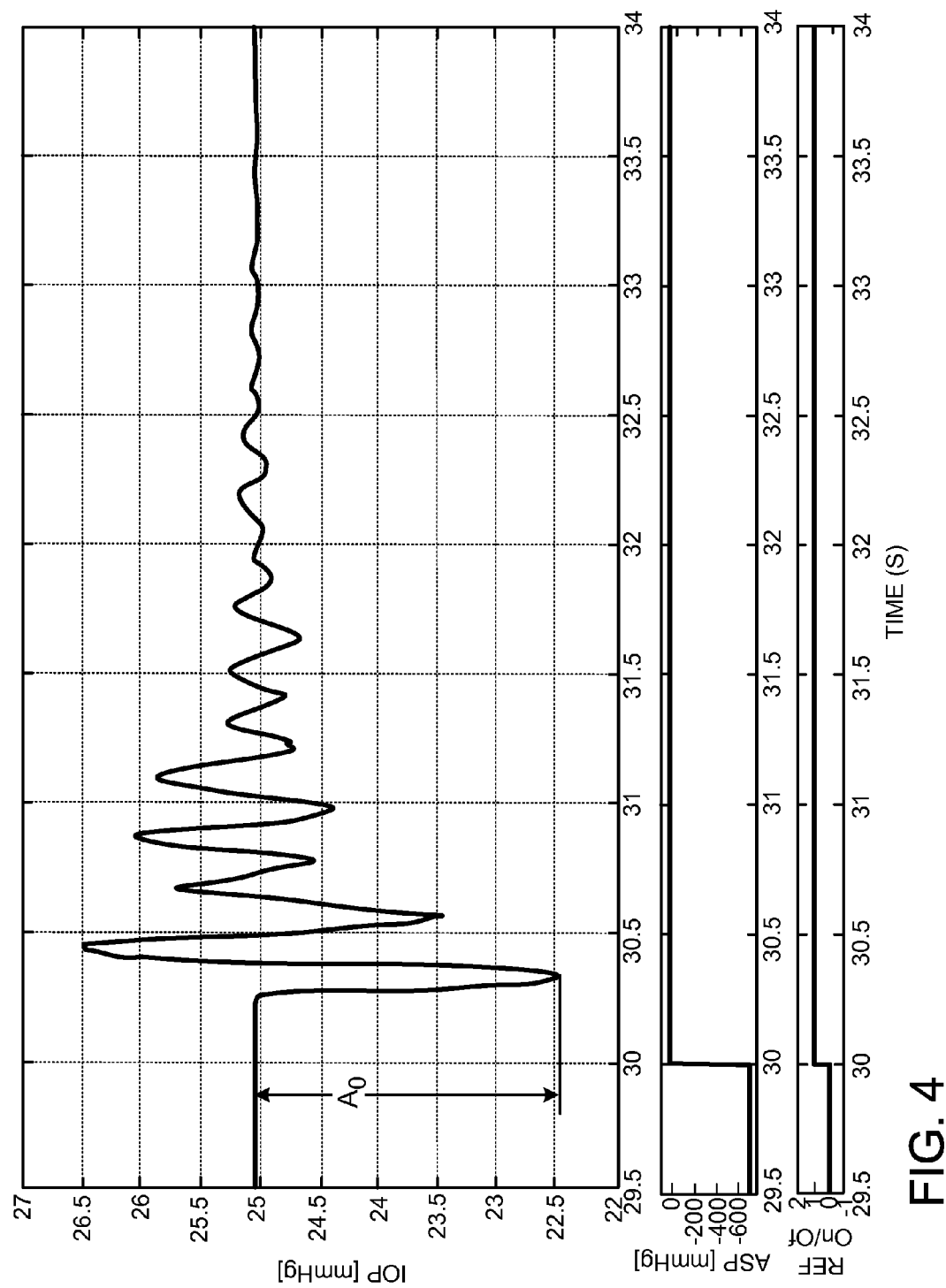
Figure 5:
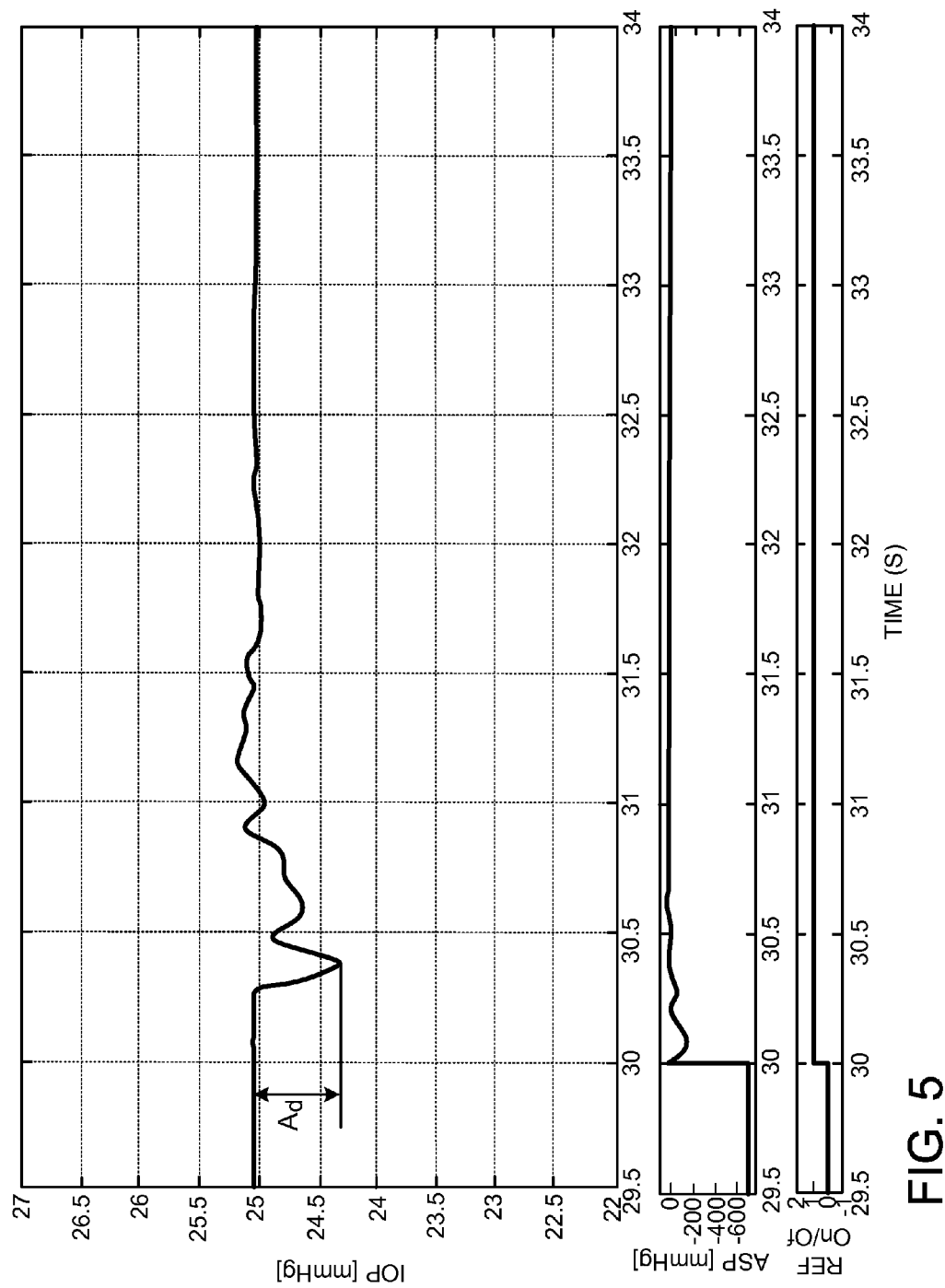
Figure 6:
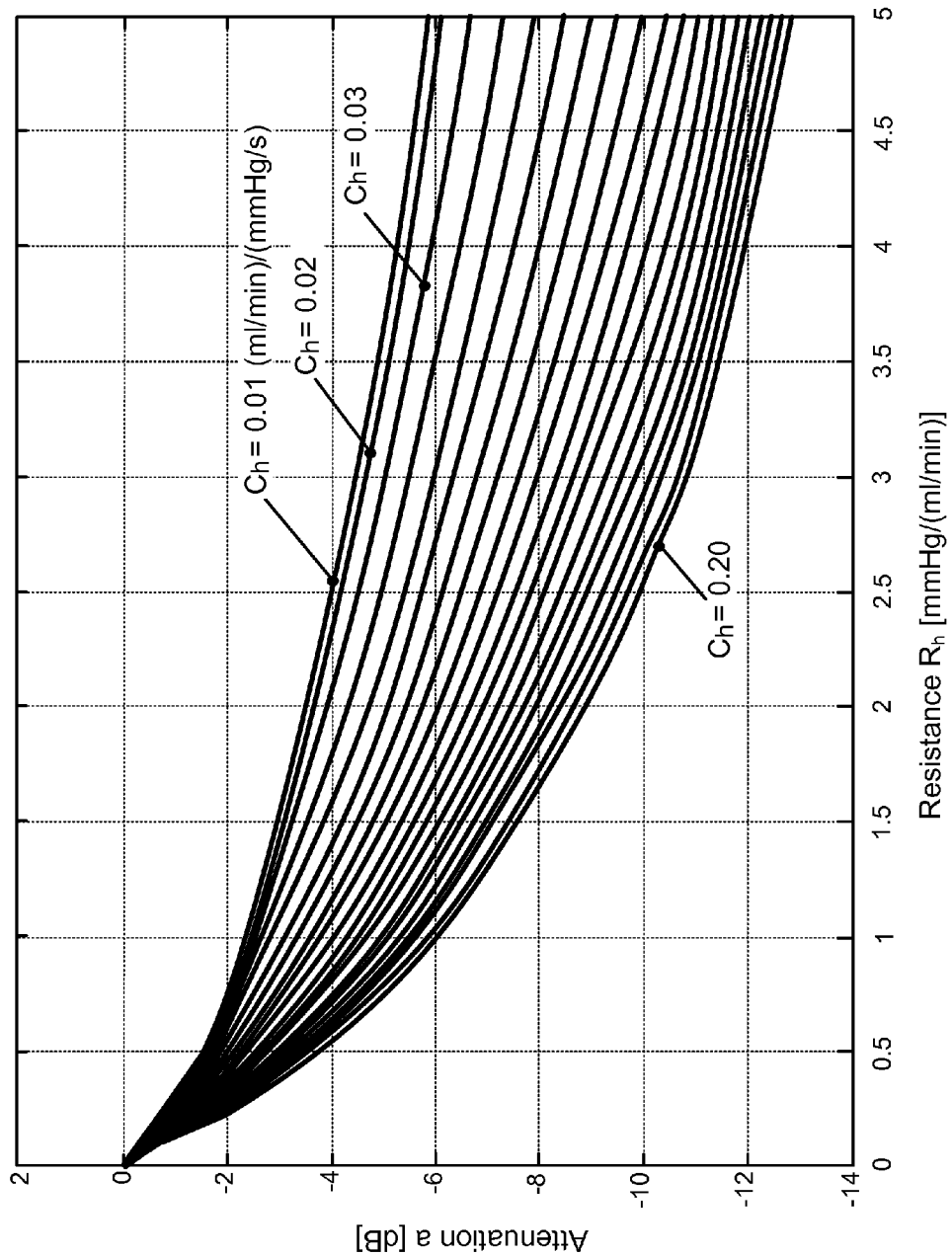

Further advantages and features of the invention are explained with reference to the attached drawings, in which:

FIG. 1 shows a schematic representation of an embodiment of the surgical system according to the invention, FIG. 2 shows another schematic representation of the embodiment of the surgical system according to the invention, FIGS. 3A-3C show schematic representations of several second fluid containers in a surgical system according to the invention, FIG. 4 shows a schematic representation of a fluid oscillation profile in the eye as a function of time, in accordance with the prior art, FIG. 5 shows a schematic representation of a fluid oscillation profile in the eye as a function of time, according to the invention, FIG. 6 shows a diagram of the oscillation attenuation as a function of the hydraulic resistance of the flow element, and FIG. 7 shows a table with the most important parameters of the components of the surgical system according to the invention.

FIG. 1 is a schematic representation of an embodiment of the surgical system 1 according to the invention. A first fluid container 2 contains an irrigation fluid 21 that can be fed through an irrigation line 3 and a handpiece 40 to an eye 50 that is to be treated. The handpiece 40 can be a phacoemulsification handpiece in which a vibrating tip 5 emulsifies a clouded lens of the eye 50 and the broken lens fragments are aspirated off. An irrigation valve 4, which is shown as a two-way valve in the view in FIG. 1, enables or prohibits a flow of the irrigation fluid in the direction of the handpiece 40. From the tip 5, an aspiration line 6 runs to one end of the handpiece 40 in order to transport emulsified lens fragments and fluid away from the eye 50. They are transported away by a suction pump 8 which, at its inlet 9, is connected to the handpiece 40 via an aspiration inlet line 7. A fluid pressure in the aspiration inlet line 7 is detected by a pressure sensor 11 which, in the embodiment shown in FIG. 1, is arranged between the inlet 9 of the suction pump 8 and the handpiece 40. The pressure sensor 11 can be arranged in a cassette 60. However, it is preferably provided near the handpiece 40, such that a change of pressure in the area of the tip 5 can be detected after a short distance through the handpiece 40. A change of pressure is detected even more quickly if the pressure sensor 11 detects the fluid pressure in the aspiration line 6 inside the handpiece 40. In this case, the aspiration line 6 can be understood as a front section of the aspiration inlet line 7.

The suction pump 8 conducts the lens fragments and fluid at its outlet 10 through an aspiration outlet line 12 into a collecting vessel 13.

An aspiration ventilation line 14 is connected to the aspiration inlet line 7 and is connected to a second fluid container 15. The second fluid container 15 holds a fluid 22, which can be fed into the aspiration inlet line 7 when a two-way venting valve 17 provided in the aspiration ventilation line 14 is in a suitable position. If a blockage (occlusion) occurs inside the aspiration line 6 or 7, for example at the distal end of the aspiration line in the area of the tip 5, as a result of lens fragments that are too large, and such that suction through the aspiration lines 6 and 7 is blocked, then a vacuum pressure builds up in these lines. This pressure can be detected by the pressure sensor 11. If this pressure is present for a predetermined time, a collapse of the eye can be avoided by actuating the venting valve 17 via a control unit 70 in such a way that fluid 22 from the second fluid container 15 passes into the ventilation line 14 and from there into the evacuated aspiration inlet line 7.

The second fluid container 15 is filled with a fluid 22 which, in the embodiment shown in FIG. 1, is delivered through a filling line 18. A flow element 19 is provided as hydraulic resistance in the filling line 18 and limits the through-flow of fluid. The filling line 18 is connected at one end 30 to the irrigation line 3, such that fluid 21 can pass into the filling line 18. The other end 31 of the filling line 18 is connected to the second fluid container 15, such that fluid 21 can penetrate through the flow element 19 into the second fluid container 15.

In order to permit filling of the aspiration inlet line 7 by emptying the second fluid container 15, a pressure compensation must be provided inside the container. This is achieved by more fluid flowing through the flow element 19 into the second fluid container 15. The pressure compensation is supported if a wall of the second fluid container 15 is provided with at least one elastically deformable area (see FIGS. 3A to 3C for example). This elastically deformable area can be a flexible lid on a rigid fluid container 15, or a flexible side wall. It is also possible for the whole of the second fluid container 15 to be made elastically deformable, for example as a hose or bag. When the fluid 22 is transported from the second fluid container 15 into the aspiration ventilation line 14 after the venting valve 17 is switched to an opened position, the elastically deformable area of the second fluid container 15 can contract, as a result of which the volume of fluid inside the second fluid container 15 is slightly reduced. Because of the direct connection between the second fluid container 15 and the filling line 18, more irrigation fluid 21 then flows through the flow valve 19 into the second fluid container 15, such that the latter is again filled with sterile irrigation fluid 22.

FIGS. 3A to 3C show various forms of a second fluid container 15 with at least one elastically deformable area. The fluid containers 15 are tubular, with a direct connection to the filling line 18 and to the ventilation line 14. The connection can be achieved by mechanical or chemical connecting means or by a thermal connecting method. In the form shown in FIG. 3A, the filling line 18, the second fluid container 15 and the ventilation line 14 are formed in one piece. The second fluid container 15 thereby represents a central section of greater diameter of the lines 18 and 14. In the form shown in FIG. 3B, the second fluid container 15 is a hose piece having narrowed diameters at the ends connected to the lines 18 and 14, whereas in the form shown in FIG. 3C an additional hose with corresponding reducing pieces 32 is provided. The fluid containers 15 can be produced, for example, by extrusion, blow molding or injection molding.

If fluid 22 is carried off into the ventilation line 14, the diameter in the central area of a second fluid container 15 can in each case decrease (see broken lines in FIGS. 3A to 3C).

Since the flow valve 19 has a relatively high hydraulic resistance compared to the irrigation line 3 or the aspiration inlet line 7, a fluid oscillation arising, as a result of the abrupt emptying of the second fluid container 15, in the filling line 18 and in the adjoining irrigation line 3 and thus also in the eye 50 is significantly attenuated. In FIG. 4, the upper diagram shows an oscillation profile of the intraocular pressure in the eye as a function of time according to a system in the prior art. The diagram presented below that shows the associated aspiration pressure, with the latter increasing very rapidly from −700 mmHg to almost 0 mmHg during pressure compensation. The "abrupt" venting, also called reflux, of the aspiration inlet line 7 with irrigation fluid 22 is shown in the bottom diagram in FIG. 4 as a jump function from 0 to 1. The initial amplitude of the oscillation is designated by $A_0$.

By comparison, FIG. 5 shows the instantaneous switching to venting with irrigation fluid 22 (bottom diagram), the profile of the pressure in the aspiration inlet line 7 (middle diagram), and the associated profile of the intraocular pressure (top diagram). It can be clearly seen that the initial amplitude $A_d$ is considerably lower than in a surgical system according to the prior art (see FIG. 4). With the selected parameters, the attenuation is approximately 75%, such that there is no longer any danger of collapse of the eye or of damage to the capsular bag.

FIG. 6 shows a diagram with a group of curves, where the attenuation during venting with the system according to the invention is plotted on the ordinate, and the resistance of the flow element is plotted on the abscissa. The following statements can be made on the basis of FIG. 6:

The higher the hydraulic capacitance of the second fluid container 15, the higher also is the attenuation of the fluid oscillation in the eye if the hydraulic resistance of the flow element 19 is constant.

The higher the hydraulic resistance of the flow element at a constant hydraulic capacitance of the second fluid container, the higher the attenuation of the fluid oscillation in the eye.

The attenuation is higher by a factor of 2 if, at a hydraulic resistance of 0.5 mmHg/(ml/min), the hydraulic capacitance is increased by a factor of 10 from 0.02 (ml/min)/(mmHg/s) to 0.2 (ml/min)/(mmHg/s).

The technical and mathematical relationships for the optimal configuration of the surgical system according to the invention are explained below in detail on the basis of a hydraulic simulation model. In FIG. 2, the model used is shown with symbols from electronics, the view being derived from FIG. 1. The handpiece 40, the eye 50 and the cassette 60 are shown as blocks. The model in FIG. 2 has hydraulic resistances, hydraulic capacitances and hydraulic inductances. These can be described as follows:

Hydraulic resistance $R_h$

With laminar flow in a tube, the hydraulic resistance $R_h$ of a line can be defined according to Poiseuille's law as:

$$R_h = \frac{8 \cdot \eta \cdot l}{\pi \cdot r^4}$$

In the calculation of $R_h$, the internal radius r of a tube line or hose line is entered with the reciprocal value of the fourth power. The length l of the line and the dynamic viscosity $\eta$ of the liquid are each entered linearly in the calculation of $R_h$. The hydraulic resistance of a line characterizes the pressure that has to be applied in order to convey a volumetric flow of fluid. The unit of hydraulic resistance can be expressed, for example, in [mmHg/(ml/min)].

Hydraulic inductance $L_h$

A hydraulic line has an inductance $L_h$. The hydraulic inductance characterizes the dynamic change in pressure resulting from the inertia of the volume of fluid that is to be accelerated. It can be defined by the following formula:

$$L_h = \frac{\rho \cdot l}{A}$$

The density $\rho$ of the fluid defines, with the line length l and with the internal cross section A of the line, the hydraulic inductance $L_h$, the unit of which can be expressed in [mmHg*s/(ml/min)].

Hydraulic capacitance $C_h$

The hydraulic capacitance characterizes a change in the volume of a fluid as the fluid pressure changes. The hydraulic capacitance $C_h$ can be defined by the elastic properties of the hose material or wall material of the lines $E_{wall}$ according to the following equation:

$$C_h = \frac{V_0 \cdot 2 \cdot r}{E_{Wall} \cdot h}$$

$V_0$ designates the volume of fluid enclosed by the line. The wall thickness h of the line wall and the internal radius r of the line and the elastic modulus of the elastic wall $E_{wall}$ define the capacitive properties of the elastic line. In the case of a soft silicone hose, an elastic modulus of $E_{soft}$=1 MPa is assumed, while a hard PVC or hard silicone hose is described by an elastic modulus of $E_{hard}$=3 MPa. Hydraulic capacitance has the possible unit [(ml/min)/(mmHg/s)].

Proceeding from the hydraulic capacitance $C_h$ and hydraulic inductance $L_h$ of an elastic line, the propagation velocity c of pressure waves in such a line can be defined according to the following formula:

$$c = \frac{l}{\sqrt{L_h \cdot C_h}} = \sqrt{\frac{E_{Wall} \cdot h}{2 \cdot r \cdot \rho}}$$

The unit of the wave velocity propagation or phase velocity is [m/s].

For an aspiration hose with an internal radius r=0.9 mm, which is made of PVC and has an elastic modulus $E_{wall}$=3 MPa and a wall thickness h=1 mm, this leads, with the above equations of condition, to a wave propagation velocity of c=40.8 m/s. The elastic modulus of the elastic wall material predominantly determines this phase velocity c of the pressure wave.

The propagation of a one-dimensional wave can be described with the partial differential equation of second order. It is called the wave equation or d'Alembert equation, in which the following applies:

$$\frac{\partial^2 p}{\partial t^2} = c^2 \frac{\partial^2 p}{\partial x^2}$$

The solution of the hyperbolic wave equation can be performed using numerical methods, e.g. the characteristics method. The Matlab/Simulink software from Mathworks, for example, is suitable for this purpose.

In order to calculate the pressure profile in the eye and in the aspiration inlet line, it is necessary to assume some numerical values. They have been determined and verified on the basis of experiments on model eyes. A hydraulic capacitance of $C_h$=50 (µl/min)/(mmHg/s) was determined for the eye, which corresponds to 0.83 µl/mmHg. The hydrostatic pressure from the bottle was given as p=30 mmHg.

If the aspiration line is evacuated to −700 mmHg (prestressed), a defined amount of fluid volume is required to compensate the line to the atmospheric level. The following values are used for calculating the hydraulic capacitance $C_{ASP}$ of the aspiration inlet line 7:

|  | Abbreviation | Value | Unit |
|---|---|---|---|
| Elastic modulus of wall | $E_{wallASP}$ | 3 | MPa |
| Length | l | 2 | m |
| Internal radius | $r_i$ | 0.9 | mm |
| Wall thickness | h | 1 | mm |

The hydraulic capacitance $C_{ASP}$ of the aspiration inlet line 7 is thus calculated as follows:

$$C_{ASP} = \frac{V_0 \cdot 2 \cdot r}{E_{wallASP} \cdot h} = \frac{\pi \cdot 0.9^2 \cdot 2 \cdot 2 \cdot 0.9 \cdot 60 \cdot \mu l \cdot s}{3 \cdot 10^6 \cdot 0.001 \cdot \frac{760}{101325} \cdot mmHg \cdot min} = 24.427 \ (\mu l/min)/(mmHg/s)$$

At a prestressing of −700 mmHg vacuum, this gives a compensation volume of 24.427 µl/60*700 mmHg=0.23 ml, in order to reduce the pressure in the aspiration inlet line 7.

The hydraulic capacitance $C_h$ of the second fluid container 15 is therefore preferably the same or a multiple of the aspiration line capacitance $C_{ASP}$. The hydraulic capacitance of the second fluid container 15 can be provided, for example, by a small elastic hose line with the following values:

|  | Abbreviation | Value | Unit |
| --- | --- | --- | --- |
| Elastic modulus of wall | $E_{wall}$ | 0.2 | MPa |
| Length | l | 20 | mm |
| Internal radius | $r_i$ | 2 | mm |
| Wall thickness | h | 0.5 | mm |

The hydraulic capacitance $C_h$ is then calculated as follows:

$$C_h = \frac{V_0 \cdot 2 \cdot r}{E_{wall} \cdot h} = \frac{\pi \cdot 2.0^2 \cdot 0.020 \cdot 2 \cdot 2.0 \cdot 60 \cdot \mu l \cdot s}{0.2 \cdot 10^6 \cdot 0.0005 \cdot \frac{760}{101325} \cdot mmHg \cdot min} = 80.41 \ (\mu l/min)/(mmHg/s)$$

The hydraulic resistance $R_h$ of the flow element 19 can advantageously be achieved in a simple way by a narrow line cross-section. With $R_h$=4 mmHg/(ml/min), this leads to the following calculation:

|  | Abbreviation | Value | Unit |
| --- | --- | --- | --- |
| Dynamic viscosity BSS solution | $\eta$ | $1.0 * 10^{-3}$ | $N * s/m^2$ |
| Length | l | 20 | mm |
| Hydraulic resistance of the flow element | $R_h$ | 4 | mmHg/(ml/min) |

$$r_l = \left(\frac{8 \cdot \eta \cdot l}{\pi \cdot R_h}\right)^{1/4} = \sqrt[4]{\frac{8 \cdot 1 \cdot 10^{-3} \cdot 0.020 \cdot \frac{N \cdot s}{m^2} \cdot m}{\pi \cdot 4 \cdot \frac{101325}{760} \cdot \frac{60}{10^{-6}} \cdot \frac{N \cdot s}{m^5}}} = 0.2 \ mm$$

For a length of the flow element of l=20 mm, an internal diameter d=0.4 mm is thus obtained for the flow element at a resistance of $R_h$=4 mmHg/(ml/min).

The starting situation assumed for the simulation was that the handpiece is blocked (occluded) in the aspiration line and that the pump output is interrupted. The vacuum pressure in the evacuated aspiration line is −700 mmHg. The venting valve 17 then opens, such that a pressure compensation of the aspiration line takes place. The resulting pressure oscillations of the fluid in the aspiration line and in the eye are calculated in terms of amplitude and as a function of time and are monitored until they have abated.

FIG. 4 shows the profile in a surgical system according to the prior art, in which no hydraulic resistance is arranged in the filling line and no hydraulic capacitance is arranged between filling line and ventilation line, and instead only a venting valve is provided for pressure compensation between irrigation line and aspiration line. After the valve opens, the pressure in the aspiration inlet line 7 increases very rapidly from −700 mmHg to almost 0 mmHg (see middle diagram). A few tenths of a second later, the pressure oscillation thereby caused in the irrigation line is active in the eye, with the oscillation having an initial amplitude $A_0$ (see top diagram). FIG. 5 shows the same situation, but in the surgical system according to the invention with the values calculated above. The pressure in the aspiration inlet line is stable after only about 0.6 second and has increased to 0 mmHg (see middle diagram). The pressure oscillation in the eye, however, is considerably less than in the system according to the prior art. As can be seen from the top diagram, the amplitude $A_d$ reaches only about 25% of the level of the amplitude $A_0$.

The attenuation a can be described as the Briggs logarithm from the ratio of the attenuated initial amplitude $A_d$, as is achieved in the surgical system according to the invention, and of the initial oscillation amplitude $A_0$ of the entirely unattenuated oscillation in a system according to the prior art:

$$a = 10.1 \ g(A_d/A_0)$$

At a hydraulic capacitance of the second fluid container of, for example, $C_h$>50 (μl/min)/(mmHg/s) and a hydraulic resistance of the flow element of $R_h$>2 mmHg/(ml/min), a pronounced attenuation effect of a>6 dB can be achieved according to FIG. 6.

The table in FIG. 7 shows the base data for the hydraulic simulation. The characteristic variables and the hydraulic properties are shown for each element. The irrigation line 3 is divided into a "BSS hose" from the first fluid container 2 to the junction with the filling line 18 and an "IRR hose" from the junction to the inlet of the handpiece 4. The irrigation line in the handpiece is designated as "IRR handpiece", and the aspiration line in the handpiece is designated as "ASP handpiece". These two line sections have only a hydraulic resistance (see also FIG. 2). The incision (insertion of the needle into the eye) is characterized by a hydraulic resistance "EYE R", and the eye by a hydraulic capacitance "EYE C". The aspiration inlet line from the handpiece to the pump is designated as "ASP hose". These values listed in FIG. 7 were used in the calculation for the simulation of the pressure oscillations in the eye and in the aspiration line, as shown in FIG. 5.

The invention claimed is:

1. A surgical system, comprising:
    a first fluid container configured to hold an irrigation fluid;
    a surgical handpiece;
    an irrigation line connected at a first end to the first fluid container, and which is connected at a second end to the surgical handpiece;
    a suction pump having an inlet;
    an aspiration inlet line, which is provided from the surgical handpiece to the inlet of the suction pump, such that fluid can be sucked through the handpiece by the suction pump;
    a second fluid container configured to hold the irrigation fluid;
    an aspiration ventilation line, which connects the second fluid container to the aspiration inlet line;
    a venting valve, which is provided in the aspiration ventilation line at a location between the second fluid container and the aspiration inlet line and which is configured so that a position of the venting valve can be switched as a function of a fluid pressure in the aspiration inlet line;
    a filling line connected at a first end to the irrigation line and at a second end to the second fluid container and
    a flow element provided in the filling line, the flow element having a constant hydraulic resistance of between 0.5 and 50.0 mmHg/(ml/min).

2. The system as claimed in claim 1, wherein the flow element, at a dynamic viscosity ($\eta$) of the fluid of 0.001 Ns/m², has a length (l) passed through by the fluid of less than 100 mm with a hydraulic radius ($r_i$) of less than 1.0 mm.

3. The system as claimed in claim 1, wherein the flow element is a line, channel, bore or diaphragm.

4. The system as claimed in claim 1, wherein the second fluid container has a hydraulic capacitance ($C_h$) of 0.05 to 0.2 (ml/min)/(mmHg/s).

5. The system as claimed in claim 1, wherein a hydraulic capacitance ($C_h$) of the second fluid container is at least equal to and preferably more than twice a hydraulic capacitance ($C_h$) of the aspiration inlet line.

6. The system as claimed in claim 1, wherein the filling line, at a second end, is coupled to the second fluid container by a mechanical or chemical connecting mechanism or by a connection based on a thermal connecting method.

7. The system as claimed in claim 1, wherein the second fluid container is tubular.

8. The system as claimed in claim 1, wherein at least a part of the filling line, the second fluid container and at least a part of the aspiration ventilation line are formed in one piece.

9. The system as claimed in claim 1, wherein the irrigation line has an irrigation valve.

10. The system as claimed in claim 9, wherein the irrigation valve is arranged in the irrigation line between the handpiece and the filling line.

11. The system as claimed in claim 1, wherein, during use of the system, the fluid can be carried off by the aspiration ventilation line at the bottom or near a bottom of the second fluid container.

12. The system as claimed in claim 1, further comprising a pressure sensor configured to detect the fluid pressure in the aspiration inlet line near the handpiece.

13. The system as claimed in claim 12, wherein the pressure sensor is configured to detect the fluid pressure in the aspiration inlet line inside the handpiece.

14. A method, comprising:
providing a surgical system as claimed in claim 1,
switching the venting valve, when or after a predefined vacuum pressure has been reached in the aspiration inlet line so that fluid from the second fluid container is delivered from the aspiration ventilation line to the aspiration inlet line, and
the second fluid container is filled with irrigation fluid from the first fluid container, wherein the irrigation fluid flows through the flow element in the filling line.

15. A surgical system, comprising:
a first fluid container configured to hold an irrigation fluid;
a surgical handpiece;
an irrigation line connected at a first end to the first fluid container, and which is connected at a second end to the surgical handpiece;
a suction pump having an inlet;
an aspiration inlet line, which is provided from the surgical handpiece to the inlet of the suction pump, such that fluid can be sucked through the handpiece by the suction pump;
a second fluid container configured to hold the irrigation fluid;
an aspiration ventilation line, which connects the second fluid container to the aspiration inlet line;
a venting valve, which is provided in the aspiration ventilation line at a location between the second fluid container and the aspiration inlet line and which is configured so that a position of the venting valve can be switched as a function of a fluid pressure in the aspiration inlet line;
a flow element in fluid communication with the irrigation line and the second container,
wherein the flow element has a constant hydraulic resistance of between 0.5 and 50.0 mmHg/(ml/min).

16. A method, comprising:
providing a surgical system as claimed in claim 15,
switching the venting valve, when or after a predefined vacuum pressure has been reached in the aspiration inlet line so that fluid from the second fluid container is delivered from the aspiration ventilation line to the aspiration inlet line, and
the second fluid container is filled with irrigation fluid from the first fluid container, wherein the irrigation fluid flows through the flow element in the filling line.

17. A surgical system, comprising:
a first fluid container configured to hold an irrigation fluid;
a surgical handpiece;
an irrigation line connected at a first end to the first fluid container, and which is connected at a second end to the surgical handpiece;
a suction pump having an inlet;
an aspiration inlet line, which is provided from the surgical handpiece to the inlet of the suction pump, such that fluid can be sucked through the handpiece by the suction pump;
a second fluid container configured to hold the irrigation fluid;
an aspiration ventilation line, which connects the second fluid container to the aspiration inlet line;
a venting valve provided in the aspiration ventilation line at a location between the second fluid container and the aspiration inlet line;
a filling line connected at a first end to the irrigation line and at a second end to the second fluid container; and
a flow element provided in the filling line between the irrigation line and the second fluid container.

18. The surgical system of claim 17, wherein the venting valve is configured so that a position of the venting valve can be switched as a function of a fluid pressure in the aspiration inlet line.

19. The surgical system of claim 17, wherein the flow element has a constant hydraulic resistance of between 0.5 and 50.0 mmHg/(ml/min).

20. A method, comprising:
providing a surgical system as claimed in claim 17,
switching the venting valve, when or after a predefined vacuum pressure has been reached in the aspiration inlet line so that fluid from the second fluid container is delivered from the aspiration ventilation line to the aspiration inlet line, and
the second fluid container is filled with irrigation fluid from the first fluid container, wherein the irrigation fluid flows through the flow element in the filling line.

* * * * *

UNITED STATES PATENT AND TRADEMARK OFFICE
CERTIFICATE OF CORRECTION

PATENT NO. : 8,317,739 B2  
APPLICATION NO. : 12/740213  
DATED : November 27, 2012  
INVENTOR(S) : Christoph Kuebler Page 1 of 1

It is certified that error appears in the above-identified patent and that said Letters Patent is hereby corrected as shown below:

<u>Sheet 4 of 7, (y-axis),</u>  
FIG. 4, delete "ON/OF" and insert --ON/OFF--

<u>Sheet 5 of 7, (y-axis),</u>  
FIG. 5, delete "ON/OF" and insert --"ON/OFF--

<u>Sheet 7 of 7,</u>  
FIG. 7, delete "resistence" and insert --resistance--

<u>Column 1,</u>  
Line 9, delete "benfit" and insert --benefit--

<u>Column 7,</u>  
Line 28, delete "length/" and insert --length *l*--

<u>Column 9,</u>  
Line 36, delete "resistanceof" and insert --resistance of--

<u>Column 10,</u>  
Line 60, delete "container and" and insert --container; and--

Signed and Sealed this  
Second Day of April, 2013

Teresa Stanek Rea  
*Acting Director of the United States Patent and Trademark Office*